(12) United States Patent
Griffin

(10) Patent No.: US 9,678,275 B1
(45) Date of Patent: Jun. 13, 2017

(54) EFFICIENT COUPLING OF INFRARED RADIATION TO RENAL CALCULI

(71) Applicant: InnovaQuartz LLC, Phoenix, AZ (US)

(72) Inventor: Stephen E. Griffin, Peoria, AZ (US)

(73) Assignee: InnovaQuartz LLC, Phoenix, AZ (US)

( * ) Notice: Subject to any disclaimer, the term of this patent is extended or adjusted under 35 U.S.C. 154(b) by 0 days.

(21) Appl. No.: 15/161,939

(22) Filed: May 23, 2016

(51) Int. Cl.
*G02B 6/26* (2006.01)
*G02B 6/36* (2006.01)
*A61B 18/22* (2006.01)
*A61B 18/26* (2006.01)

(52) U.S. Cl.
CPC ........... *G02B 6/262* (2013.01); *G02B 6/3624* (2013.01); *A61B 2018/2233* (2013.01); *A61B 2018/266* (2013.01)

(58) Field of Classification Search
CPC .............................. G02B 6/262; G02B 6/3624
See application file for complete search history.

(56) References Cited

U.S. PATENT DOCUMENTS

| | | | |
|---|---|---|---|
| 5,454,807 A | 10/1995 | Lennox et al. | |
| 5,685,824 A | 11/1997 | Takei | |
| 6,246,817 B1 | 6/2001 | Griffin | |
| 6,282,349 B1 * | 8/2001 | Griffin | G02B 6/3813 385/81 |
| 6,802,838 B2 | 10/2004 | Loeb et al. | |
| 6,953,458 B2 | 10/2005 | Loeb | |
| 7,359,601 B2 | 4/2008 | Loeb | |
| 7,909,817 B2 | 3/2011 | Griffin et al. | |
| 8,417,079 B2 * | 4/2013 | Hayasaka | G02B 6/3834 385/15 |
| 8,529,561 B2 | 9/2013 | Griffin et al. | |
| 8,932,289 B2 | 1/2015 | Mayse et al. | |
| 9,005,195 B2 | 4/2015 | Mayse et al. | |
| 9,017,324 B2 | 4/2015 | Mayse et al. | |
| 2007/0165981 A1 * | 7/2007 | Tanaka | G02B 6/327 385/33 |
| 2014/0074072 A1 | 3/2014 | Griffin et al. | |

* cited by examiner

*Primary Examiner* — Ryan Lepisto
(74) *Attorney, Agent, or Firm* — Synthesis Intellectual Property LLC

(57) ABSTRACT

Herein are disclosed protected optical fiber terminations for use in the treatment of renal and biliary calculi. The protected optical fiber termination including a ferrule affixed to the optical fiber that provides the termination of the optical fiber with protection from contact with saline and/or biological fluids. The optical fiber termination can include open or closed ferrules. The open ferrules providing a means for maintaining a bubble, e.g., a Moses bubble on the termination; the closed ferrules providing a calumniated focus on the renal or biliary calculi.

17 Claims, 9 Drawing Sheets

DETAIL

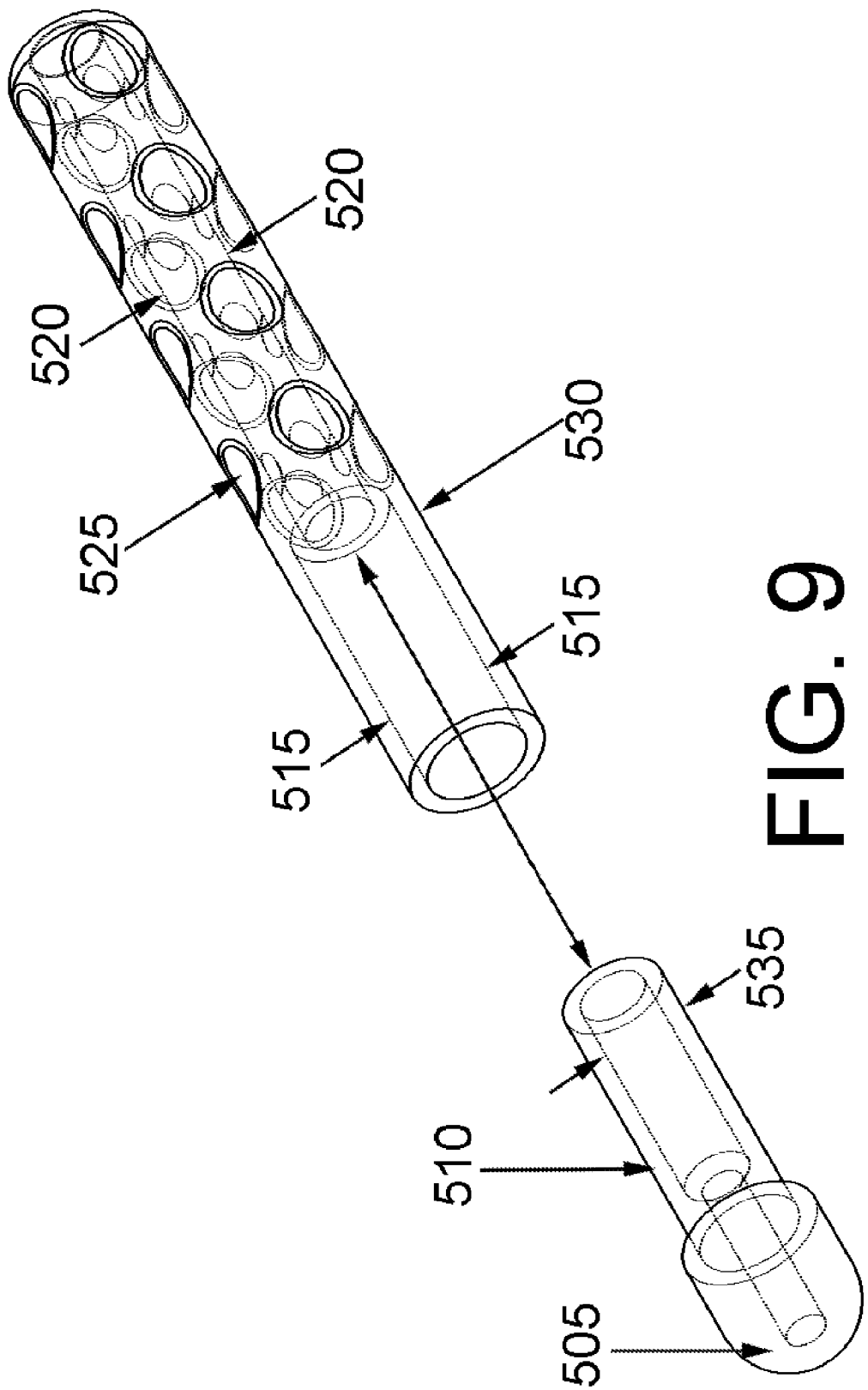

EFFICIENT COUPLING OF INFRARED RADIATION TO RENAL CALCULI

FIELD OF THE INVENTION

Fiber optic devices for fragmenting renal and biliary calculi with improved energy delivery through absorbing matrices are disclosed. The concepts discussed may find utility in other surgical procedures using axial and side firing fibers, and for non-surgical uses of infrared lasers delivered by fiber optics operating within highly absorbing fluidic matrices, such as laser induced breakdown spectroscopy (LIBS) in groundwater.

BACKGROUND

Pulsed infrared lasers that produce radiation within the wavelength range of approximately 1.5 µm to 2.2 µm are particularly useful for minimally invasive fragmentation of concretions that form within tissues and organs, owing to the relatively strong absorption by urinary and biliary calculi, and the ability to deliver said wavelengths in relatively high energy pulses by means of standard silica clad, silica core optical fiber. These same wavelengths, produced by both pulse and CW mode lasers, also find utility for ablating or vaporizing soft tissues.

Surgical techniques using infrared laser energy delivered by silica optical fiber are also hindered by strong absorption by water. As described in Isner, et al., in "Mechanism of laser ablation in an absorbing fluid field", *Lasers Surg. Med.*, 8(1988): 543-554, as the 'Moses Effect', and often referred to as the 'Moses bubble', a steam bubble is formed between the emitting face of the optical fiber and the target in aqueous media, the formation and maintenance of which consumes a substantial portion of the laser energy provided. Only the laser energy that passes through the preformed steam bubble, without encountering liquid water, imparts the target tissue.

For example, a 200 µm core optical fiber (placed 1 mm away from a kidney stone, in a saline irrigated environment) will produce a Moses bubble with a volume of about 0.1 µl within the first several dozen or hundred microseconds of a holmium laser pulse. Assuming the saline is at physiological temperature (the initial temperature affects the result minimally) almost 0.4 J is required to vaporize this volume of water. A 200 µm core laser lithotripsy fiber is typically used with laser average power settings at or under 20 W, where individual laser pulse energies range from around 0.45 J to 2.0 J, such that 20% to 90% of each pulse may be consumed simply in forming the bubble. Larger diameter fibers delivering higher energy pulses do not fare much better, and some fare worse, given that the volume of saline vaporized essentially squares with the fiber diameter.

Estimating losses due to boiling saline (with a 1 mm fiber to target separation and assuming full divergence at the maximum fiber NA, within pure water), a standard 273 µm core fiber loses about 0.5 J, a 365 µm core fiber loses almost 0.75 J, and 550 µm core fiber is diminished by about 1.25 J where a 910 µm core fiber loses about 2.6 J, just to create the steam bubble. The maximum laser pulse energy is limited for most holmium lasers to 5 J although the latest models offer a bit larger pulse energies. Once a Moses bubble is formed, the fiber tip is operating within what is essentially an air environment and the central portion of the beam passes to the target virtually unimpeded; the refractive index elevation and absorptivity due to steam have only minor effect. Some portion of the energy at the phase boundary of the bubble is consumed in maintaining the Moses bubble for the remainder of the pulse duration which ranges from 250 µs to 350 µs for typical holmium lasers and up to 700 µs and longer in some models. The higher angle energy is the least effective in ablating tissue, but there are thermal degradation modes for stones that are aided by even low quality light, e.g. spontaneous fracture due to differential thermal expansion in the polycrystalline matrix. As a general rule one prefers that the laser energy delivered within the confines of the endosurgical field is used to do work rather than boil water.

Accordingly, standard practice in laser lithotripsy calls for the fiber tip to be held in direct contact with the calculus, thereby minimizing energy lost to boiling water. Such intimate contact is virtually impossible to maintain for the duration of surgery, however, and there may be undesirable consequences to this practice as well. Fibers held in contact with stones appear to degrade more rapidly in a failure mode that has been coined "burn back" in the field of laser ureteroscopy. Urological surgeons routinely must remove small core fibers from the ureteroscope to reprocess the output tip during a surgical session or suffer dramatically reduced coupling efficiency via a severely damaged fiber tip. The consensus in the field is that tip damage is a result of physical impacts by particulate calculi ejected during the stone ablation process.

A similar problem exists for side fire fibers in soft tissue ablation, but with more serious consequences; if a side fire fiber is used in direct contact with soft tissue in holmium surgery, the fiber protective cap becomes frosted and pitted and must often be discarded and replaced in order to complete the surgery. Side fire fibers cannot be reprocessed intraoperatively. Providing for side fire fibers to be used with fixed separation from tissue and shielding the fiber from contact have been focuses of prior art in side fire fiber technology.

U.S. Pat. No. 5,454,807 (Lennox, et al.) teaches the provision of a coaxial coolant flow, gaseous or liquid, for prevention of surface tissue damage to irradiated tissue for the stated reason of permitting the application of more laser energy to underlying tissues to improve, for example, exogenous chromophore activation in photodynamic therapy (PDT).

U.S. Pat. No. 5,685,824 (Takei) teaches a "prostascope" provisioned with a standard working channel to accept an optical fiber and deliver irrigant, but where a reflector is positioned within a side opening for redirecting laser energy laterally with respect to the scope longitudinal axis: a side firing scope, if you will.

U.S. Pat. No. 6,246,817 (Griffin) teaches a reduced divergence output fiber that is ferrule reinforced for improved longevity in cryptoscopic laser lithotripsy.

U.S. Pat. No. 6,802,838 (Loeb, et al.) teaches a side firing fiber housed within a nested, dual coaxial lumen device whereby cooling fluid is passed about the side fire fiber within the central lumen and exits a common port and where coolant fluid and debris are evacuated via the same port through the second, surrounding lumen.

U.S. Pat. No. 6,953,458 (Loeb) teaches a coaxial coolant channel about an axial fiber where a gas and laser energy exit a common port, where the channel may be angled for access to orthogonally situated tissues, the gas being utilized to produce a substantially fluid free optical path for the laser radiation to reach target tissues.

U.S. Pat. No. 7,359,601 (Loeb) is a continuation-in-part of Loeb '458 teaching adaptations for standard side-firing fibers as well as bare, bevel-tipped side fire fibers.

U.S. Pat. No. 7,909,817 (Griffin, et al.) discloses a dual cap side fire fiber where the side fire function is provided within the inner, thin walled cap and the physical protection function is performed by the thicker, outer cap with cooling provided by irrigation fluid flow between the two caps during surgery. This technology will not function in the infrared region that is of interest to the current invention (due to Moses bubble formation within the confined space interfering with continuous fluid flows) but at 532 nm on the GreenLight XPS™ laser, it is the most widely used side fire fiber to date: American Medical Systems' MoXy™ fiber (AMS is currently a part of Boston Scientific and owns the preceding trademarks). U.S. Pat. No. 8,529,561 (Griffin, et al.) is a divisional of Griffin '817 describing methods for disrupting laminar flow within the annular, coaxial fluidic conduit. U. S. Pat. Pub. No. 2014/0074072 (Griffin, et al.) is a continuation-in-part of Griffin '561, teaching rotation of the outer, secondary capsule during surgery.

U.S. Pat. Nos. 8,932,289, 9,005,195 and 9,017,324 and a couple of dozen published applications (Mayse, et al.) teach cryogenically cooled tissue ablation devices for treatment of chronic obstructive pulmonary disease with various forms of energy, preferably radio frequency energy, but including laser energy, where cryogenic coolant is delivered via a lumen to a balloon, within which, or about which, resides the energy delivery electrode or presumably an optical fiber or fibers.

Coaxial cooling of fiber tips with gas flow has a long history in the laser surgical fiber design discipline. As early as the 1980s, "gas-cooled" Nd:YAG fibers were produced and sold by Lasersonics, US Surgical, and others for 'open surgery' applications, (typically non-endoscopic and no irrigation) such as found in the ear, nose and throat (ENT) specialization, where a circumferential sheathe of gas protected fiber output tips operating in air from blood and tissue ejecta contamination. A niche market remains for these fibers even today, e.g. the Gas/Liquid-Cooled Fiber sold by LightGuideOptics (Germany) and the model DSLF-60 Gas Sheathed Laser Fiber made by Laser Peripherals (Minnesota). Other applications for passing gases and liquids across fiber surfaces or over tissues also appear in the prior art, e.g. cooling tissue in cosmetic and other non-ablative laser procedures to permit more laser interaction with target chromophores (tattoo ink, spider veins, port wine stains and activation drugs for PDT, where the coolant is provided coaxially or by some other means.

In endosurgical applications of lasers, most of the cooled fiber prior art is concerned with side firing fibers for laser vaporization of the prostate or axial firing fibers for prostate enucleation. Loeb, et al. '838 teaches a side fire fiber that is housed within the lumen of a needle having a side port for the laser radiation to exit. Sterile irrigation fluid flows within the needle in an annulus about the central cylinder occupied by the side fire fiber and exits through the same port within the needle as the laser energy. This apparatus is housed within the lumen of a second tube that provides communication between a vacuum source and the area immediately outside of the needle exit port. In recovering the added volume of irrigation fluid from the surgical site, more fluid flow is possible and the fiber may be used in surgical procedures with closer confines and far smaller fluid reservoirs, such as laser discectomy. '838 further teaches that the provided suction removes suspended tissue debris from the surgical field: debris that could otherwise adhere to the side firing fiber transmissive surface. The opposite may be experienced in practice; suction about the laser output port pulls floating debris from the adjacent surgical site preferentially toward the fiber transmissive surface, amplifying tissue adhesion and ultimately leading to catastrophic fiber failure.

Griffin '817 addresses the issues of fiber damage and loss of laser energy to Moses bubble formation with a two-fold strategy: reduction of the volume of water in the column between the fiber output and the surgical target via a terminal, lens-ended up-taper for reduced divergence and a hermetically fused silica ferrule about the up-taper for increased mass at the fiber to target contact. A problem with the art taught in '817 is that it is incompatible with the size limitations for applications of the most damage susceptible fibers. The divergence reduction strategy requires the diameter of the fiber to be locally substantially increased, over a length of a centimeter or more. The delicate taper section (bare fiber) requires protection by a surrounding silica ferrule of even more substantial diameter and greater length than the bare taper segment to house the taper. (Boston Scientific opted to forego the use of a protective silica ferrule about the bare fiber segments in AccuTrac™ and Flexiva™ TracTip fibers and, instead, re-coats the bare fiber with a sacrificial polymer substance. The resulting fibers are compatible with ureteroscope working channels but the longevity of the tips is little improved (Kronenberg, et al., in "Lithotripsy performance of specially designed laser fiber tips", *J Urol.*, 195-5(2015): 1606-1612).

A fiber for use in the infrared where water and blood strongly absorb the laser energy is taught by Loeb ('458), where gas is passed about a fiber for the purpose of displacing interfering fluids as depicted in FIG. 1. Per standard practice, the optical fiber 35 resides within the lumen of a sheath 30 having a bore that is considerably larger than the fiber 35 and where the end of sheath 15 and the output face of the fiber 10 terminate substantially within a common plane. A gas supply 25 is provided to the sheath lumen via a T or Y fitting 20 or the like and flow is adjusted such that the output face 10 of the fiber may be held in contact or near contact with tissue, while a cloak of gas 45 displaces the irrigation fluid (or other fluid, such as blood) at the immediate surgical site. As such, the emitted laser radiation 40 passes to the tissue via an optical path substantially free of absorbing irrigant or blood.

A problem with the invention taught by Loeb (FIG. 1) is that, unless the sheath forms a gas-tight or nearly gas-tight seal with the target tissue, considerable gas flow is required to prevent intrusion by interfering fluids and, if the flow is sufficient to displace the inflow of fluids at the surgical site, such flow also displaces the irrigation volume as a whole, emptying the surgical site. Reducing the irrigation presence about the fiber at the surgical site also reduces some of the fluid flow function: cooling and cleaning the fiber tip to forestall optical and physical damage. Additionally, the rigid or semi-rigid sheath made of steel, rigid polymer, shape-memory alloy, and like materials, as taught by Loeb is opaque or at best translucent and, as such, obscures visualization of the surgical effect of the laser fiber such that any seal between the tissue and sheath, even a leaky seal, must periodically be broken to access surgical progress and for surveillance of routine complications such as open and bleeding arteries.

Loeb extends the application of air-sheathing to side firing fibers in '601, teaching bare, bevel-tipped side fire fibers—absent the ubiquitous transparent protective cap—and claiming that the low refractive index of the sheathing gas (carbon dioxide under continuous flow) is sufficient for preserving conditions required for total internal reflection (TIR) according to Snell's law, even where the fiber is used in an aqueous environment. While flows of sufficient volume and pressure to exclude moisture from contaminating the refractive index barrier necessary for TIR is theoretically feasible, such volumes and pressures are not compatible with the confined and tissue-bound space of the endosurgical environment. The carbon dioxide (or other "biocompatible gas") flow necessary to continuously displace the surgical irrigant from the side fire optical path is problematic as no mechanism for removing the deployed gas is provided.

Simply relying upon the gas to bubble past the irrigation flow within the cystoscope working channel is likely inadequate. Surgical interventions can take hours: e.g. for relief of the symptoms of benign prostatic hyperplasia (BPH). Where the surgical site is the prostatic urethra, adjacent to the urinary bladder, the pressures within the urethra may rise sufficient to open the interior sphincter, inflating the bladder. Further flow then fills the ureters and ultimately the kidneys where fatal consequences due to gas perfusion into the extensive capillary bed are possible. Perfusion into capillaries exposed by the surgery itself could be problematic enough on its own. While some portion of the optical path may be free of water during some portion of energy delivery events with sheath gas flows compatible with BPH surgery, total displacement of irrigant from the optical path is improbable. Were Loeb's inventions to be adapted to axial firing fibers intended for use in the kidney—the focus of the invention disclosed herein—gas perfusion into the capillary bed of the kidney would be extremely problematic.

Two prior art patents and the patent application by Griffin, et al. disclose numerous embodiments for coaxial cooling of side fire fibers that avoid problems of earlier designs, as manifest in the commercial success of an embodiment of the device sold for the vaporization of hyperplastic prostate tissue with green laser light. Green light resides within the biological or optical window, where water is essentially transparent such that there is no benefit to excluding irrigation fluids from the optical path from fiber to tissue and Griffin makes no effort to do so.

The plethora of patent applications and issued patents by Mayse, et al., deal with cooling energy delivery devices for use in an air environment—the lungs—and while a mention of the potential for use of a laser as an energy source does appear, the overriding concern of these disclosures is with cooling about, or concurrent with, application of radio frequency energy via an electrode (antenna) and has no real bearing on the invention disclosed herein.

SUMMARY

The principal losses of therapeutic infrared laser energy in laser surgery within aqueous media are due to the interaction between that energy and the media separating the fiber output surface from the target tissue or calculus; fiber optic designs for displacing the highly absorbing media within the optical path are disclosed. A simple cylindrical sheath, bonded about the output tip of a lithotripsy fiber and extending distally beyond the fiber output surface, is sufficient for capturing and providing a gas bubble along the bulk of the optical path between the fiber and the target calculus prior to laser activation. A key to the utility of this approach is provision of conditions favorable for the maintenance of the surface tension energy barrier at the gas to fluid interface (and gas to wet target interface).

Where water does intrude into the optical path within the sheath (or sleeve, or ferrule), another embodiment utilizes simple and non-toxic water-sensitive chemicals or blend to produce fresh gas to displace the water, e.g. the classical Alka-Seltzer blend of citric acid and sodium bicarbonate.

Alternatively, the water column may be replaced by non-aqueous fluidic media, transparent to infrared radiation, and provided coaxially about the fiber tip to displace the bulk of aqueous media within the optical path; for example, 3M's Fluorinert™ fluorocarbon fluids are low viscosity, largely immiscible with water, non-toxic and broadly transparent. Mixing or other disruption of the non-aqueous column is minimized by containment within the hollow cylindrical sheath that protrudes a short distance beyond the fiber exit surface.

A further option is to fill the hollow cylinder beyond the fiber tip with a transparent solid material that is more resistant to damage when in contact with calculi and/or soft tissues. A short sapphire fiber segment or similar hard solid is considered.

One embodiment is an optical fiber output termination that includes an optical fiber having a core composed of fused silica or doped fused silica, a cladding disposed about the core, a first polymer coating disposed about the cladding, and a second polymer coating disposed about the first polymer coating, an output terminus, and a stripped terminus coincident with the output terminus, the stripped terminus including the core, cladding, and the first polymer coating, a stripped terminus length, and an outside diameter; and a ferrule affixed to the stripped terminus, having a length longer than the stripped terminus length, and a borehole, the borehole having a first bore with an inside diameter substantially similar to the outside diameter of the stripped terminus, where an output face carried on the output terminus is within the bore of the ferrule, the output face positioned at a fiber setback relative to a terminus of the ferrule at a distance where the highest angle of emitted radiation does not impinge upon the ferrule borehole.

Another embodiment is an optical fiber output termination that includes an optical fiber having a silica core, a cladding disposed about the core, a first polymer coating disposed about the cladding, and a second polymer coating disposed about the first polymer coating, the second polymer coating having an outside diameter, an output terminus, and a hydrophilic-stripped terminus coincident with the output terminus, the hydrophilic-stripped terminus including the core and cladding, a hydrophilic-stripped terminus length, and an outside diameter; a ferrule affixed to the stripped terminus, having a length longer than the hydrophilic-stripped terminus length, and a borehole, where an output face carried on the output terminus is within the borehole of the ferrule, the output face positioned at a fiber setback relative to a terminus of the ferrule at a distance where the highest angle of emitted radiation does not impinge upon the ferrule borehole, the borehole having a first bore and a second bore, the first bore having an inside diameter substantially similar to the outside diameter of the hydrophilic-stripped terminus, the second bore having an inside diameter substantially similar to the outside diameter of the second polymer coating; and a moisture-sensitive, gas-generating charge that is in fluidic communication with the output terminus of the fiber, carried between the ferrule and the optical fiber.

Still another embodiment is an optical fiber output termination that includes an optical fiber having a silica core, a cladding disposed about the core, a first polymer coating disposed about the cladding, and a second polymer coating disposed about the first polymer coating, the second polymer coating having an outside diameter, an output terminus, and a stripped terminus coincident with the output terminus, the stripped terminus including the core and cladding, a stripped terminus length, and an outside diameter; a ferrule consisting of sapphire, affixed to the stripped terminus, having a length longer than the stripped terminus length, and a borehole, where an output face carried on the output terminus is within the borehole of the ferrule, the output face positioned at a fiber setback relative to a terminus of the ferrule, the ferrule carrying a lens having a flat input surface adjacent to the borehole and a convex or flat output surface; wherein the fiber output face and the ferrule lens provide a beam path that culminates at a position immediately distal to the ferrule lens.

BRIEF DESCRIPTION OF THE FIGURES

For a more complete understanding of the disclosure, reference should be made to the following detailed description and accompanying drawing figures wherein:

FIG. 4A depicts the embodiment in use where FIG. 4B depicts the embodiment between uses.

FIG. 6 is an embodiment utilizing a supplied fluid for displacing absorbing media, wherein FIG. 6A depicts a cross-section of the embodiment, FIG. 6B depicts the exterior of the embodiment, and FIG. 6C depicts an end view of the embodiment.

FIG. 9 is an isometric and exploded view, less the optical fiber of an embodiment illustrating the use of an optional crimp ferrule.

While specific embodiments are illustrated in the figures, with the understanding that the disclosure is intended to be illustrative, these embodiments are not intended to limit the invention described and illustrated herein.

DETAILED DESCRIPTION

Figure 1:
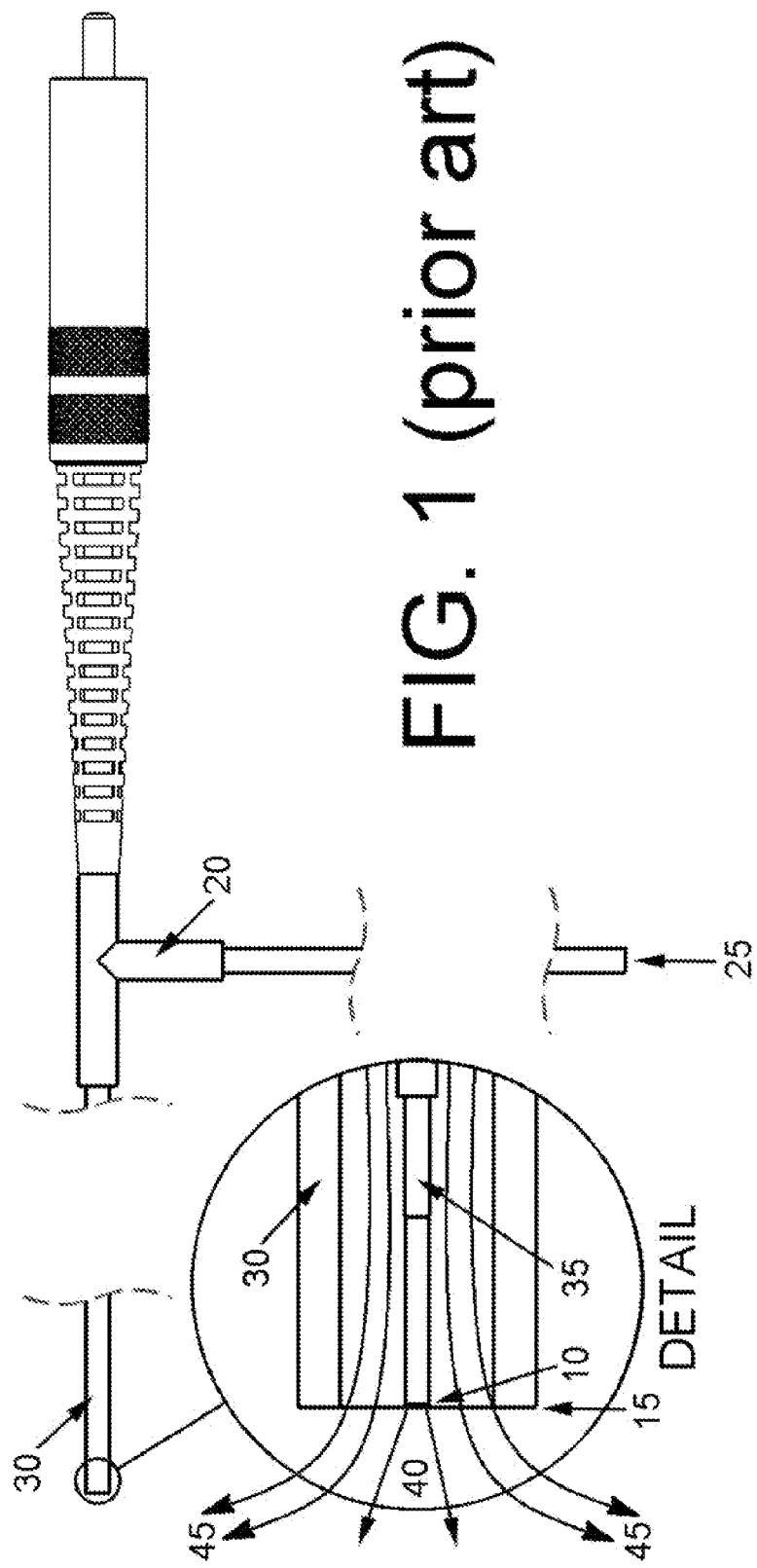
FIG. 1 depicts the concepts taught in prior art (Loeb '458) for a liquid-cooled surgical fiber.
Figure 2:
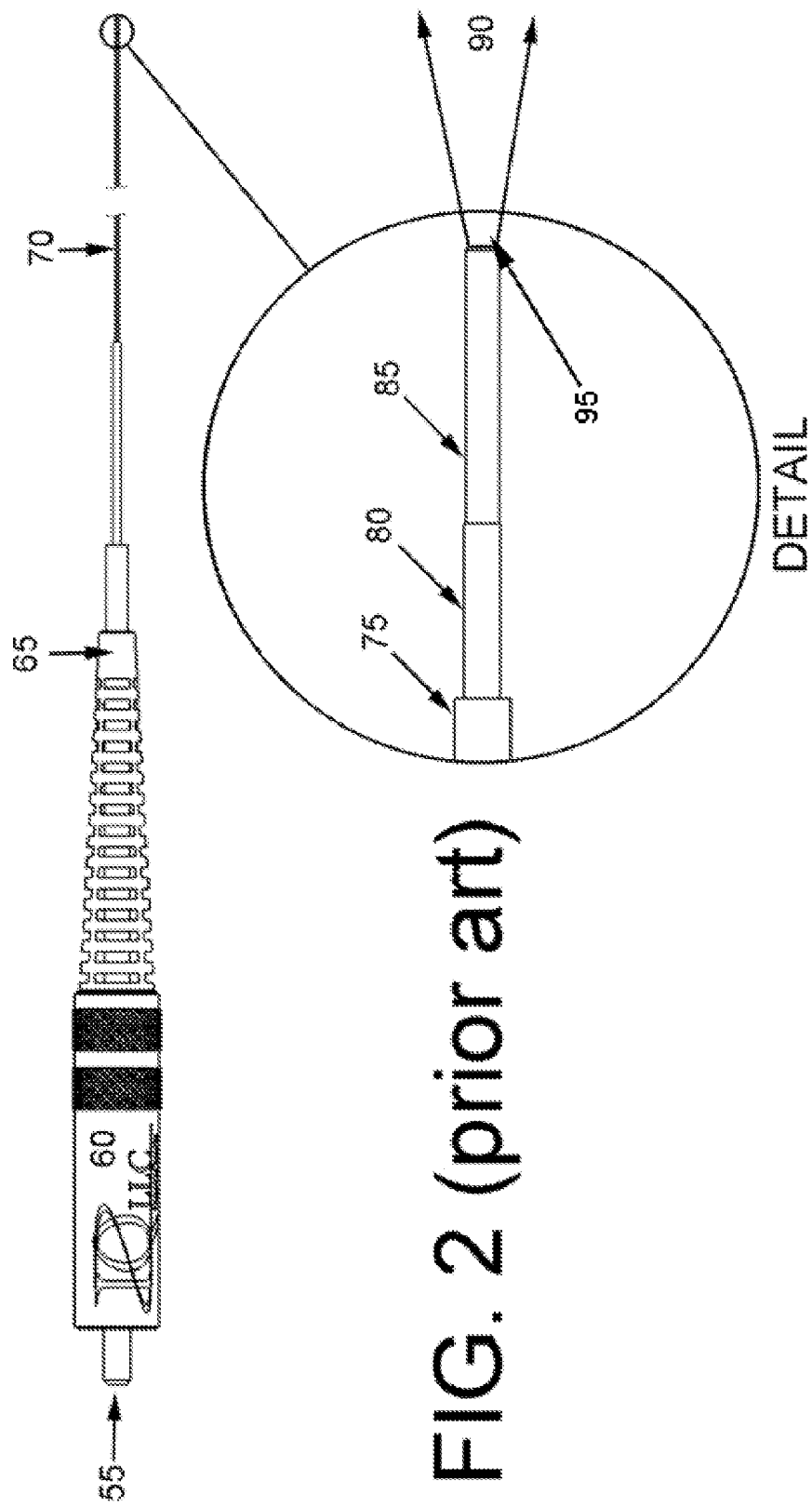
FIG. 2 is an industry standard 0.2 mm core laser lithotripsy fiber.

The simplest embodiment of the invention is a modification of prior art for laser lithotripsy as depicted in FIG. 2, the deficiencies of which are related to the susceptibility of the fiber tip 95, particularly for smaller core fibers. For orientation, a silica core, fluorine-doped silica clad 85, fluoroacrylate 80 coated and ETFE 75 (ethylene tetrafluoroethylene copolymer) buffered optical fiber 70 is housed within a laser connector 60 and laser energy is provided to the fiber at 55. A rubber boot 65 and/or layered heat shrink tubing provides bend limitation at the back of the connector 60. Laser energy is emitted from the tip in a frustoconical volume 90 where the divergence half angle is approximately 13 degrees (arcsine of the fiber numerical aperture). This latter parameter, the divergence angle, is somewhat controversial with some claiming the angle is lower due to the higher refractive index of the working environment: saline. This is true for wavelengths of laser energy that do not interact significantly with saline, but for the wavelengths most commonly used for laser lithotripsy, a steam bubble is formed between the fiber output face 95 and the target where the steam has a refractive index that is essentially the same as that of air. With the fiber operating in steam, the divergence is essentially the same as it is operating in air.

Small core fiber tips degrade rapidly in use when addressing calculi in a process referred to as "burn back" in the interventional urology art. Burn back rates appear to be proportional to pulse energies in holmium laser lithotripsy but this observation may be an artifact; initial damage to the fiber output face may be independent of pulse energy where the consequences to the damaged fiber tip are more dramatic at higher pulse energies as more energy is back-scattered. Stone ablation rates suffer greatly after onset of fiber tip damage.

The source of tip damage initiation has not been determined but it is highly probable that the onset is similar in cause to damage to other types of fibers that have been better characterized: side fire fibers. In side fire fibers, transmissive surface damage initiates due to tissue adhesion about the output on the protective cap. Where the energy density of the distorted semi-Gaussian beam profile is insufficient for vaporizing tissue, tissue adheres, forming a ring about the higher irradiance center of the output spot. This ring of tissue cooks, then carbonizes, absorbing the sub-therapeutic laser energy in the beam periphery more strongly as it blackens and transferring that heat to the protective cap.

Fused silica protective caps have low thermal conductivity such that the conducted heat is highly localized and temperatures about the output spot raise enough to lower the viscosity of the amorphous silica such that, in combination with intercalating alkali metal ions and counterions, water, etc., the silica rearranges structurally to energetically favorable crystalline form: high cristobalite; this is devitrification. Crystalline silica is birefringent so the optical transmission characteristics subtly change, but the more likely problematic change to the cap is crystallite formations that scatter the laser energy, may slough off, etc. distortion the output beam profile further and further, amplifying the progression of devitrification, ad infinitum until a pit if formed in the protective cap at the output.

As discussed in the background section, aqueous irrigant used in urological surgery absorbs roughly 40% of infrared laser radiation at as little as 1 mm separation between the fiber and the target. Contact with tissue or calculi initiates damage to the fiber and reduces efficient coupling of laser energy to the target by roughly 40% within minutes. It is impossible to precisely control fiber to target distance with endoscopic visualization and manual control. Accordingly, surgeons place the fiber tip in direct contact with the calculus to minimize the energy lost to boiling water. While calculi are not organic tissue, per se, they often contain organic crystals and, when primarily inorganic, stones often harbor considerable organic waste in boundaries between crystals so a similar damage onset cause is probable. Even absent carbonization, direct contact between the fiber tip and material under laser ablation causes the local temperature increase necessary for devitrification onset. Once the tip is damaged the conditions for accelerating devitrification improve and provide the positive feedback loop described for side fire fiber pitting discussed above.

Figure 3:
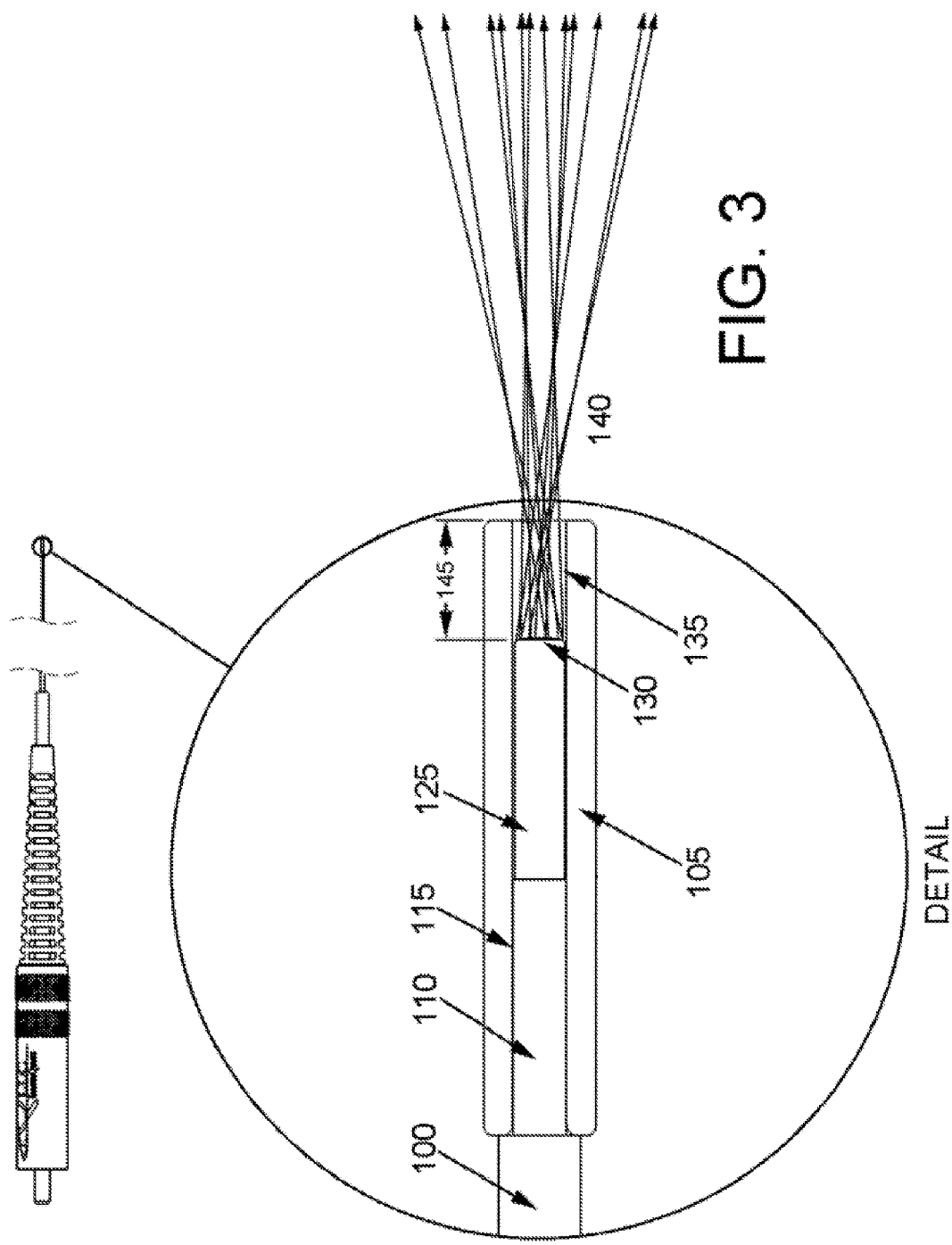
FIG. 3 depicts the essential components of the invention.

FIG. 3 depicts a simple embodiment of a solution to this problem: a ceramic, glass, polymer or metal ferrule 105 is mounted on the fiber tip at the fluoroacrylate coating 110 with adhesive 115. The ferrule 105 serves two functions: establishing a fixed and short stand-off from the target and excluding saline infusion into the optical path 135. The embodiment illustrated in FIG. 3 provides as a simple retrofit of the standard laser lithotripsy fiber depicted in FIG. 2. In FIG. 2, the bare glass clad 85 portion of the fiber tip is illustrated as it appears after test firing in air, if somewhat exaggerated in length, in anticipation of the consequent bare fiber section 125 thought probable to result from test firing the new art in air after addition of the ferrule 105. (100% of surgical fibers are functionally tested on surgical lasers prior to sterilization as part of the quality system at InnovaQuartz LLC.) The ferrule includes a borehole that is preferably a longitudinal, centrosymmetric opening in the tube/ferrule. As used herein, the borehole can include a plurality of sections or regions. A single section may be referred to a bore, whereas a plurality of sections/regions can be distinguished based on the inside diameter (ID) of the borehole and are referred to as a first bore, a second bore, and/or a third bore, or other distinction that clearly indicates the differences between the sections/regions based on ID.

While adhesion to the ETFE buffer 100 of the fiber is difficult, adhesion to the fluoroacrylate fiber coating 110 is not a great deal better and, being opaque, a ceramic, metal or polymer ferrule 105 makes inspection of the coverage of the adhesive 115 in the bond impossible. Further, for adherence to basic engineering principles, at least two methods of retaining the ferrule on the fiber is preferred, particularly where the consequences of ferrule detachment are problematic; a considerable surgical time would be spent in attempting to retrieve a lost ferrule from minor renal calices where it could seed formation of additional kidney stones.

Small fibers are used in laser lithotripsy because larger fibers are incompatible with the flexible ureteroscopes needed to reach stones in the kidney, particularly the 'lower pole stones' that gravity favors. Working channels are typically 3.6 Fr or just over a millimeter in diameter. While it is possible to pass a 365 µm core fiber through a 3.6 Fr channel, the 0.8 mm to 1 mm ETFE jacketed fiber blocks irrigation flow almost entirely and the stiffness of the 0.4 mm glass fiber (1.1 cladding to core ratio) restricts the deflection of the scope to near inutility.

273 µm core fibers (generally known as 272 µm core, due to an early rounding error) are the largest that are commonly used with flexible ureteroscopes when addressing renal calculi. The typically 0.45 mm ETFE outer diameter allows passage of sufficient irrigation for maintaining clarity in the surgical field but the 0.3 mm glass fiber does restrict scope deflection sufficiently to make accessing lower pole stones extremely difficult with the fiber preloaded in the working channel. Boston Scientific's AccuTrac™ and Flexiva™ TracTip 242 µm core fibers are designed to pass through the working channel while it is fully deflected, eliminating fiber rigidity related reduction in scope deflection, at least for initial placement of the fiber (the fibers are designed to pass the deflected working channel one time, only). The slightly up-tapered and lens-ended fiber tip of the Boston fibers also reduce divergence in the area immediately adjacent to the fiber output and the larger emission diameter, and likely the absence of sharp edges, forestalls burn back with less than 2 mm loss of length being reported for typical lithotripsy cases. In reality, however, the Boston Scientific fibers (1.2 CCDR, or cladding to core diameter ratio) are little more flexible than a standard 273 µm core fiber (1.1 CCDR) and recent reports from the field indicate that burn back continues to be a major concern in ureteroscopic lithotripsy (URS).

The area immediately adjacent to the fiber emission face is the area where most energy is lost to the Moses Effect. It is impossible to hold a fiber perfectly flat against an irregular kidney stone surface such that at least some portion of the energy must vaporize water in transit to the stone surface, and the fraction of the laser energy lost increases proportionally with pitting of the calculus by ablation and geometrically with fiber output face damage.

200 µm core fibers, such as depicted in FIGS. 2 and 3, are the most commonly used fibers for accessing lower pole kidney stones because they permit full deflection of all scopes when preloaded within the working channel. Burn back in 200 µm is a considerable problem and the damage typically begins within the first 2 minutes of lasing. When the fiber burns back to the ETFE buffer, many surgeons will consider removing the fiber and for intraoperative reprocessing: strip the ETFE jacket and cut a new fiber output face. Smaller core fibers, e.g. 150 µm core, are even more susceptible to burn back, and larger core fibers, e.g. 273 µm core, are also susceptible to burn back, although somewhat less so.

The techniques used to perform this reprocessing are generally crude and far from optimal, generally involving cutting the fiber with scissors. Nicks to the fiber are commonly produced due to the use of inappropriately sized fiber strippers, damaged stripper blades (high carbon steel blades start to rust even before the first use, due to autoclave sterilization) or an almost ubiquitous use of improper technique. Tips detaching on reintroduction through even a somewhat relaxed working channel is a common complaint. Passing a working channel with a sharply edged, freshly cut fiber under any deflection risks the tip penetrating the working channel liner (typically a thin walled fluoropolymer) or at least generating pits and scratches that harbor waste and bacteria inaccessible to disinfection and passing these materials on to the next patient (ureteroscopes cannot be sterilized). (Efforts at educating surgical personnel in proper fiber reprocessing techniques have largely failed.)

Patients under general anesthesia suffer higher risk with time under anesthesia such that time in the OR should be kept to a minimum. OR time also costs a great deal of money and is typically billed by the minute. The extension of a surgical session due to the almost immediate loss of optimum fiber to target coupling efficiency, removing and reprocessing fiber tips or simply removing and reloading fibers, repositioning the ureteroscope, chasing after detached fiber tips, etc. generally exceeds the total lase time.

The fiber depicted in FIG. 3 also slightly focuses the laser energy 140 due to a curved output face 130, enabling a close fitting ferrule 105 to be used without blocking the higher angle rays of the otherwise immediately diverging output. Air is trapped in the hollow space produced by the fiber setback 145 within the ferrule and this bubble is maintained throughout insertion of the fiber into the saline-filled surgical field due to the very strong barrier that the surface tension creates at such small dimensions.

Setback 145 is illustrated at approximately the maximum attainable without spatially filtering or 'clipping' the emitted beam 140 of the 200 µm fiber depicted and to provide a reservoir for air. In use, the ferrule 105 of the fiber is maintained in contact with the target so that it gets hot, albeit not as hot as the much smaller, bare fiber where ceramic, polymer or glass ferrules are employed. Metal ferrules may get hot enough to melt the fiber buffer material 100 and/or damage the adhesive bond, promoting tip detachment. Under any heating, the air bubble captured in the open bore of the ferrule 135 expands and some air may be lost as a result. When the fiber is at rest, cooling, the smaller amount of air occupies a smaller volume within the open bore 135, generally predicted by using Charles' law to estimate the gas expansion assuming the expanded gas is all lost:

$V1/T1=V2/T2$

V1 is the volume of the open bore, T1 is physiological temperature in Kelvins, V2 is the expanded volume T2 is the maximum temperature reached. The result of this simple exercise is less than 25% of the gas bubble is lost for every 100 degree (centigrade) temperature rise, independent of the initial volume, and less than 20% total, if one assumes cooling by the surrounding irrigation flow keeps the temperature at or under 100° C.

Where fluid does intrude into the bore of the ferrule during periods of rest, it is displaced upon the first pulse on next activation but it will return between pulses (unless the pulse rate is faster than the collapse of the Moses bubble—rates unachievable using existing holmium lasers) but will not return where CW lasers are used until cessation of lasing. The mass of water that must be vaporized with each pulse in a second (and subsequent) treatment session remains constant baring condensation of droplets deeper within a hydrophilic ferrule bore, therefore a hydrophobic interior surface is desirable. The mass of water vaporized is also directly proportional to the depth of the setback 145, so minimization of setback is also desirable.

Figure 4:
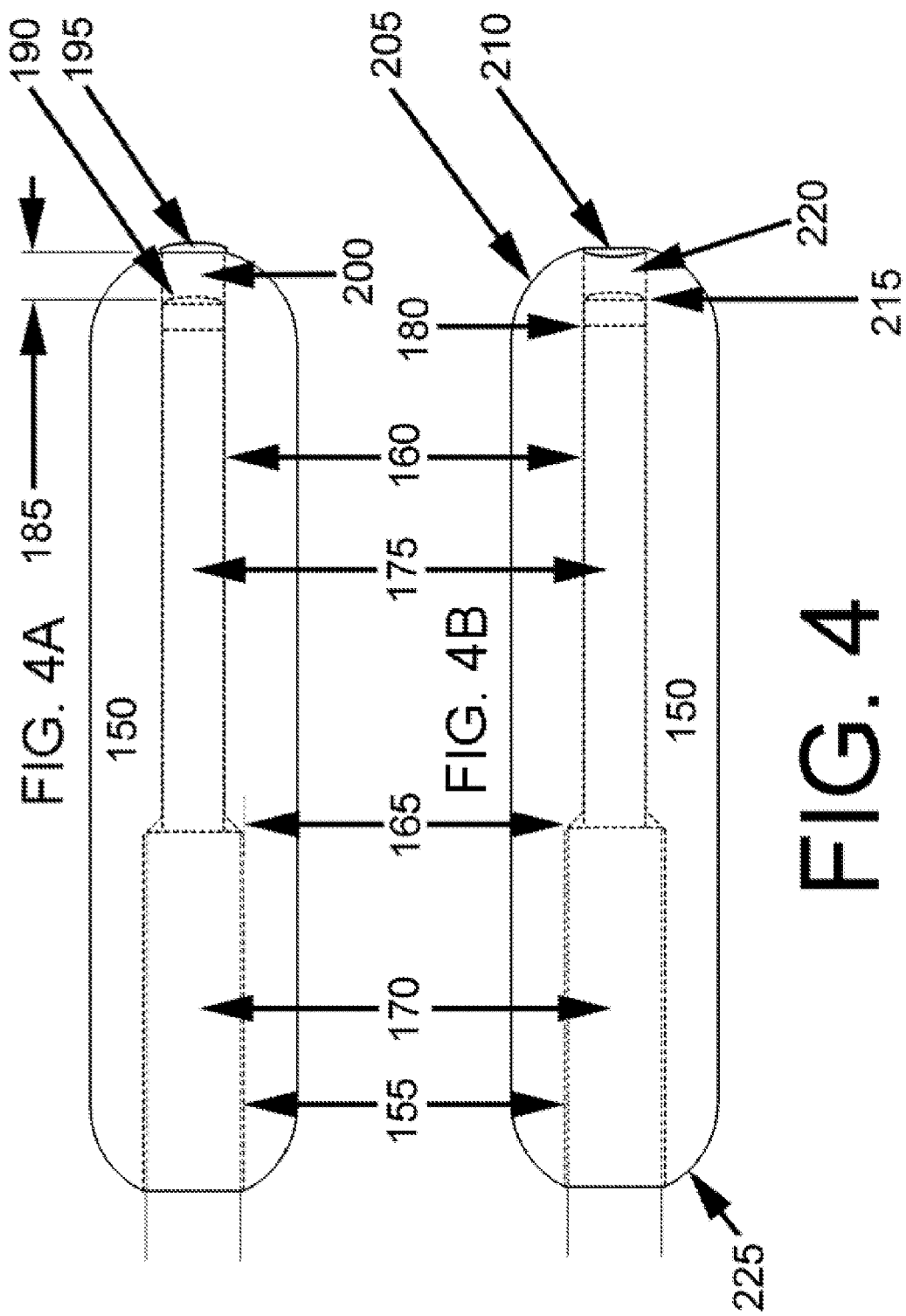
FIG. 4 is a preferred embodiment of the invention reliant upon naturally captured gas to displace absorbing media.

FIG. 4 illustrates a preferred embodiment of a fiber tip equipped with a fused quartz ferrule 150 with minimal setback 185, at approximately 0.25 mm, where post-production functional testing was performed in water rather than air such that the burn back 180 of the hydrophobic fluoroacrylate (FA) coating 175 is minimized and due solely to the formation of the slight convex lens 190 on the fiber tip 215 and the Fresnel reflections thereby produced. FIG. 4A depicts the air bubble 200 slightly protruding 195 prior to first laser activation and FIG. 4B depicts the air bubble 220 with approximately 15% of the volume replaced by water 210 prior to a subsequent laser treatment session (and following reaching about 100° C. in the first session).

Features of the device are a hydrophobic and rounded surface 205 where the ferrule 150 contacts the kidney stone, a hydrophobic surface within the setback volume 200 and 220, a rounded proximal end 225 to facilitate passage through scope channels, two different diameter bores, the larger 155 of which accommodates the nylon buffer 170, preferred for much greater adhesion with UV cure adhesives such those offered by Dymax, Norland and Electronic Materials and the smaller 160 of which accommodates the FA coated fiber 175.

Assembly is simplified by the dual diameter bore and transparent ferrule. The bare FA fiber segment is threaded into the silica ferrule and is advanced past the chamfer 165 between the bore diameters. Just prior to the nylon entering the large bore 155, an annulus of adhesive is applied about the bare FA fiber just distal to the nylon buffer 170. As the fiber is advanced to a point where it stops, with the nylon on the chamfer 165, excess adhesive is forced into the thin cylindrical spaces between the bare FA coated fiber and the nylon buffered fiber. Inspection to verify sufficient adhesive coverage is easily performed via microscopic examination through the transparent silica ferrule (sleeve or sheath). UV light cures the adhesive through the UV transparent ferrule.

The rounded stone contact or distal end of the fiber ferrule 205 serves several purposes. It facilitates passage through even fully deflected ureteroscopes, it alters the contact angle of the meniscus at the air water barrier, supporting a protrusion of air 195 that is small enough to be sustained, even in rough handling, and it minimizes the contact and thermal conduction between the fiber assembly and the target. Partial round ends are more robust than full round ends but both options have utility when the ferrules are made of fused quartz, fused silica, borosilicate glass and alternative materials such as sapphire, zirconia, alumina and other ceramics. Metallic ferrules offer a further potential for retention on the fiber by crimping onto the fiber buffer at or about 170 but metals quite efficiently conduct heat to heat labile portions of the fiber assembly and may be of limited utility in practice.

Figure 5:
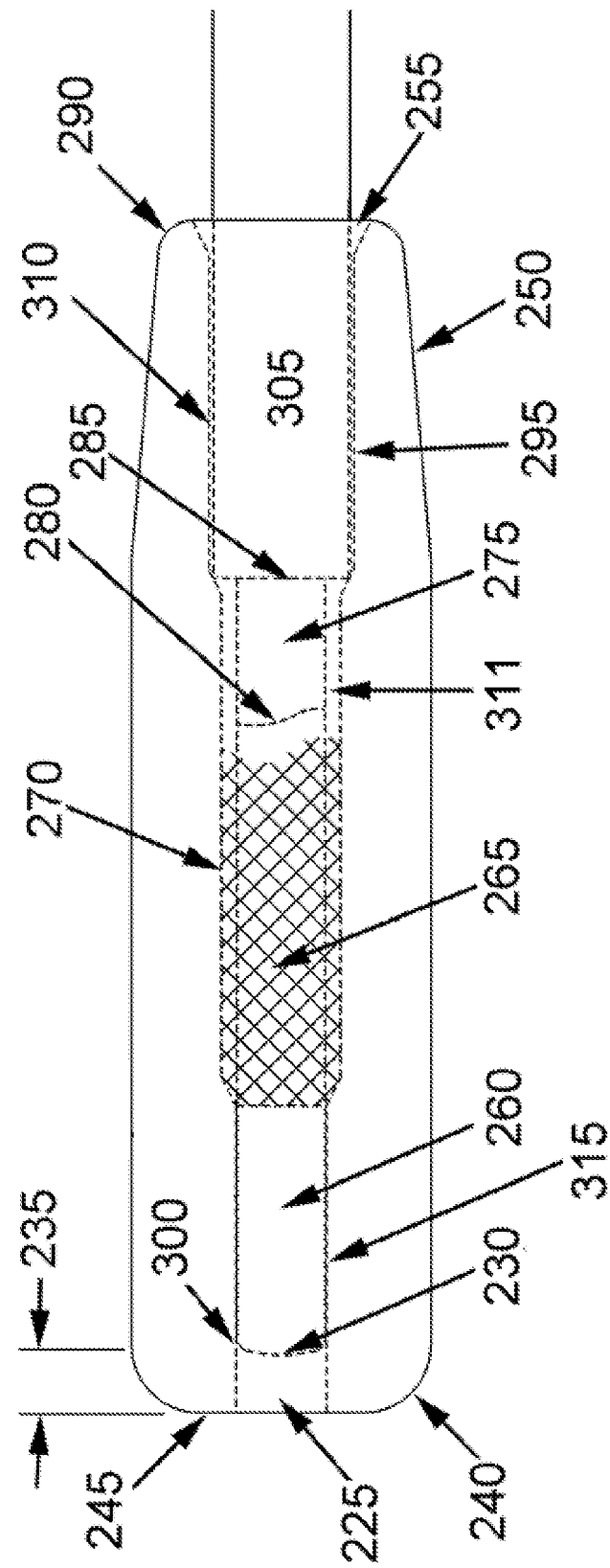
FIG. 5 is a preferred embodiment of the invention with active generation of gas for displacing absorbing media.

FIG. 5 depicts a preferred embodiment directed to replenishing the air bubble 225 should water find its way to the 'bottom of the air well'—where the end of the fiber 230 defines the depth 235 of the air bubble 225. The ferrule (or sleeve) in this embodiment is ½ rounded or filleted 240 at the stone contact face 245 to permit smooth passage through the working channel under full deflection while presenting a more robust interface with the stone than that depicted in FIG. 4. The rear or fiber insertion end 250 of the ferrule is chamfered 255 on the outer diameter to reduce the surface area of contact with the working channel liner and chamfered 255 on the inner diameter to facilitate threading the delicate, bare fiber 260 into the ferrule and for loading of a moisture-sensitive, gas-generating charge 265 (e.g., a stoichiometric mixed bed of citric acid and sodium bicarbonate or other biocompatible gas generating compounds, e.g., those described in U.S. Pat. No. 3,556,803 and incorporated herein by reference in its entirety) within a space provided by an intermediate bore diameter 270. The proximal end of the ferrule is also rounded 290 to provide for smooth passage of the fiber in removal.

The fiber FA coating 275 has been removed from the distal portion of the fiber 260, terminating 280 just distal to the edge 285 of ETFE or nylon buffered fiber. Adhesive fills the void 310 between the buffered fiber 305 and the large bore 295 of the ferrule and part of the void 311 between the intermediate bore diameter 270 and the FA coated 275 and bare fiber 260, up to the mixed bed of gas generating compounds 265. In use, where saline intrudes to the bottom of the well at the outer circumference 300 of the fiber tip, it wicks between the bare fiber 260 and the small bore 315 of the ferrule, by capillary action, until it encounters the gas generating bed 265. Upon contact with liquid water, the gas generation bed produces gas ($CO_2$ in the case of the sodium bicarbonate citric acid mix). The gas generated displaces the water and refills the air bubble well 225.

For laser lithotripsy, the local heat generated in ablating the kidney stone—this invention is primarily directed to kidney stones and gall stones as opposed to ureter stones or bladder stones although the embodiments taught herein, and larger scale embodiments thereof, may find applications in other surgeries such as soft tissue ablation—has proven sufficient to initiate burn back wen confined to small and bare fiber tips. Thermal issues are typically far more problematic for soft tissue surgery application of optical fiber, particularly where the fiber may be encrusted with carbonized tissue or become inadvertently buried in tissue (or purposefully so). For higher temperature uses like soft tissue ablation, ceramic, sapphire or other refractory material ferrules are clearly superior to the fused quartz or fused silica and alternative geometries may prove superior. Sapphire ferrules' transparency, lack of susceptibility to devitrification and refractory qualities may also offer simplified and reliable assembly and superior longevity when used on the small fibers typically used URS.

Figure 6:
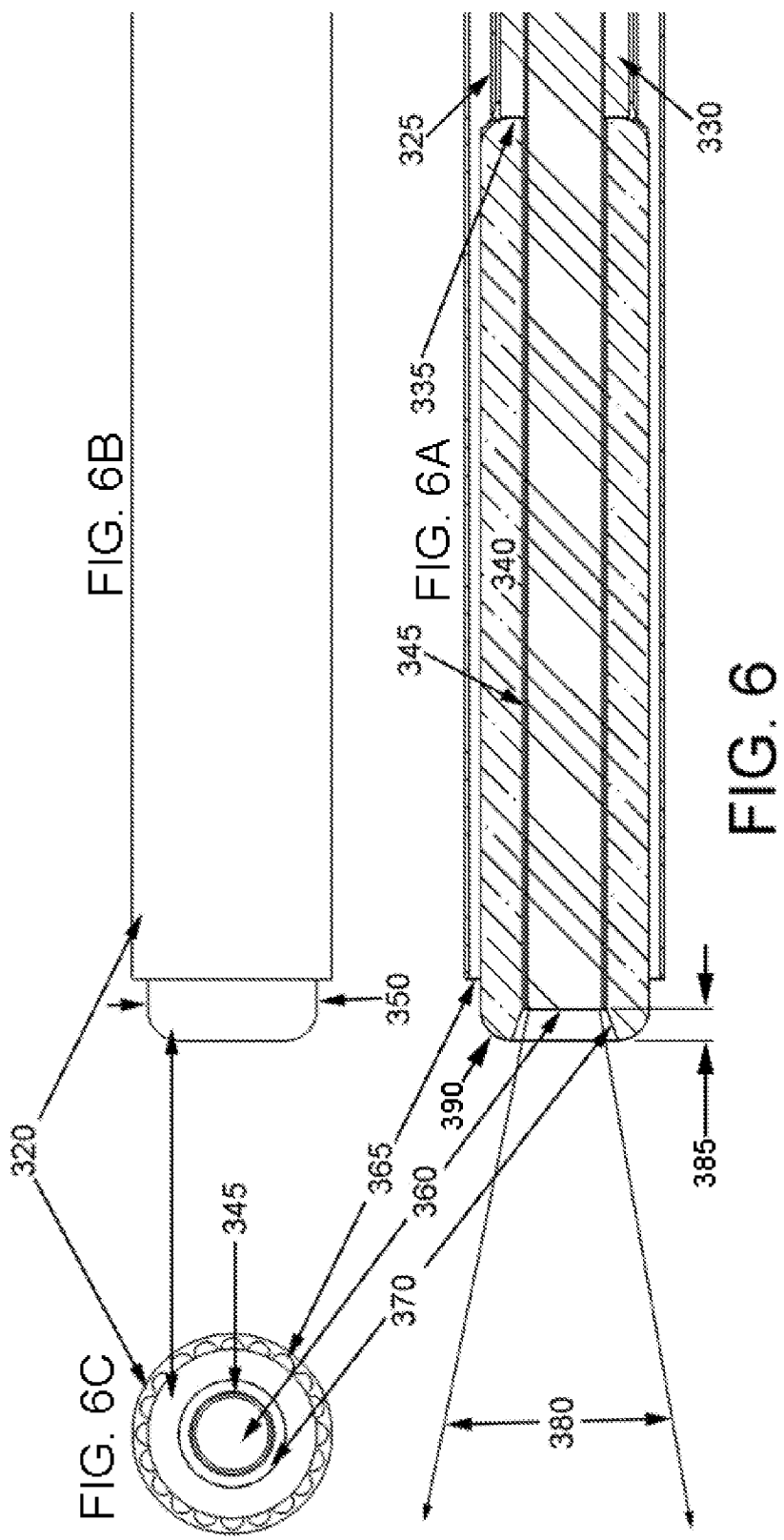

For kidney stone applications with access via flexible ureteroscope, working channel space limitations preclude the addition of coaxial fluid communicating conduits in most cases, particularly where significant flows are necessary for the function. An embodiment of the invention that remains dimensionally compatible with the just over 1 millimeter lumen of the working channel is illustrated in FIG. 6. Some flexible ureteroscopes have working channels smaller than 1 mm, e.g. a dual 3.3 Fr channel scope from Richard Wolf, within which even the embodiment depicted in FIG. 6, with an outer diameter of 0.65 mm could restrict the flow of irrigation too much.

The fluidic delivery embodiment utilizes a ceramic ferrule 340 because materials such as alumina are less likely to fracture with the thin walls that are required for space considerations; in this case, for reference, the bore of the ceramic ferrule is just slightly larger than the FA coating 345 diameter of the standard 200 μm core fiber (240 μm glass clad, 260 μm FA coating 345, 400 μm ETFE buffer 330) with an outer diameter 350 of 0.55 mm. The fiber in this instance is shown as mechanically flat polished at the output face 360 and the inherently hydrophobic FA coating 345 remains intact. Flat polished fibers of the type used in holmium laser lithotripsy are 0.22±0.02 NA (numerical aperture). The divergence of these fibers is therefore approximately 0.22 radians so that a flat polished fiber emitting energy at maximum divergence cannot be set back within a closely matching bore any appreciable distance 385 without some of the energy contacting the bore wall.

In illustrating the fluidic delivery embodiment (FIG. 6), the setback 385 depicted is approximately the maximum that it could be give the divergence 380 of the output, were the outlet end of the ceramic ferrule not chamfered 370, but in order to avoid chamfering the output end of the ferrule, the fiber centricity within the FA coating 345 and FA coating centricity within the bore of the ferrule would have to be very close to perfect, as would the setback distance, to avoid losing any energy at all in absorption by the ferrule 340. In that one of the fundamental goals of the invention is to minimize losing precious laser energy in heating not target materials, particularly saline, chamfering the ferrule is a reasonable precaution where flat output fibers are used.

The ceramic ferrule is ½ rounded (filleted) 390 on each end. The fluid transfer tube 320 is a multilumen and thin wall structure of polymer such as polyimide, e.g. HD Microsystems Pyralin P12542, a fluoropolymer such as FEP, or other polymer with a large central lumen 325 slightly larger than the ETFE buffer 330 diameter of the fiber, surrounded by a plurality of small lumen 365. The distal end of the multilumen tube 320 is counterbored to accommodate the ceramic ferrule diameter and the proximal end of the ferrule 340 seats in the multilumen tube 325 where the ETFE buffer abuts 335 the ceramic ferrule 340.

Fluid is passed thorough the plurality of small lumen 365 about the circumference of the central lumen 325, communicating with the multilumen tube by way of a T or Y fitting, located between approximately 50 cm from the distal terminus and proximal terminus of the device, as known in the art. The fluid delivery lumens are partially obstructed by the ceramic ferrule within the counterbored multilumen tube, producing a localized pressure rise that is a function of the fluidic supply parameters and fluid viscosity.

The purpose of providing the fluid to the laser emission end of the device is to displace the saline irrigation just about the fiber and preferably substantially between the fiber and the target, with an infrared transparent, non-toxic, biocompatible material, preferably of low viscosity and with a density greater than water/irrigant saline. Potential candidate liquids meeting these requirements are the Fluorinert electronic heat transfer fluids made by Minnesota Mining and Manufacturing.

Alternatively, it may be desirable to utilize a coaxial fluid conduit such as depicted in FIG. 6 in the reverse: suction applied to the T or Y fitting to remove stone dust and debris from the surgical field.

The preceding embodiments can include an open or exposed fiber output face (e.g., 130 in FIGS. 3 and 190 in FIG. 4) where an air bubble or the Moses bubble prevents the interaction of the saline and/or biological fluids with the fiber output face. Preferably, biological fluids do not contact the fiber output face. To improve the retention of the air bubble or Moses bubble at the fiber output face, the ferrule can include a hydrophobic or super-hydrophobic surface. The hydrophobic or super-hydrophobic surface is preferably located on the external output surface and within the bore, preferably, covering the internal setback surface, in one instance, the hydrophobic surface is includes within the borehole (preferably covering the setback surface). The hydrophobic or super-hydrophobic surface can, for example, include a fluorosilane (e.g., the condensation product of an organosilane ($R^f$—$Si(OR')_3$) with a silica surface), a nanoparticle surface (e.g., a nanotexture film), or a patterned surface (e.g. a nanotexture) whereby the coating or surface structure provides the desired hydrophobicity. In one instance, the desired hydrophobicity can be expressed in terms of a saline contact angle, the contact angle is preferable greater than 90°, 100°, 110°, 120°, 130°, or 140°. As described above, the utilization of the laser can heat the quantity of gas within the setback volume (e.g., 200 and 220 in FIG. 4) which may decrease during firing (bubble loss); upon cooling this decrease in quantity (temperature and pressure) can lead to water entering the setback volume (compare FIG. 4A and FIG. 4B). Preferably, the hydrophobic or super-hydrophobic setback surface provides a contact angle of at least 90°, 100°, 110°, or 120° even when the pressure within the setback volume is decreased due to quantity loss. Even more preferably, the hydrophobic or super-hydrophobic setback surface prevents deflection of saline or biological fluids into the setback volume (i.e. the surface meniscus is collinear with the ferrule output face or deflects outward from the ferrule output face).

Figure 7:
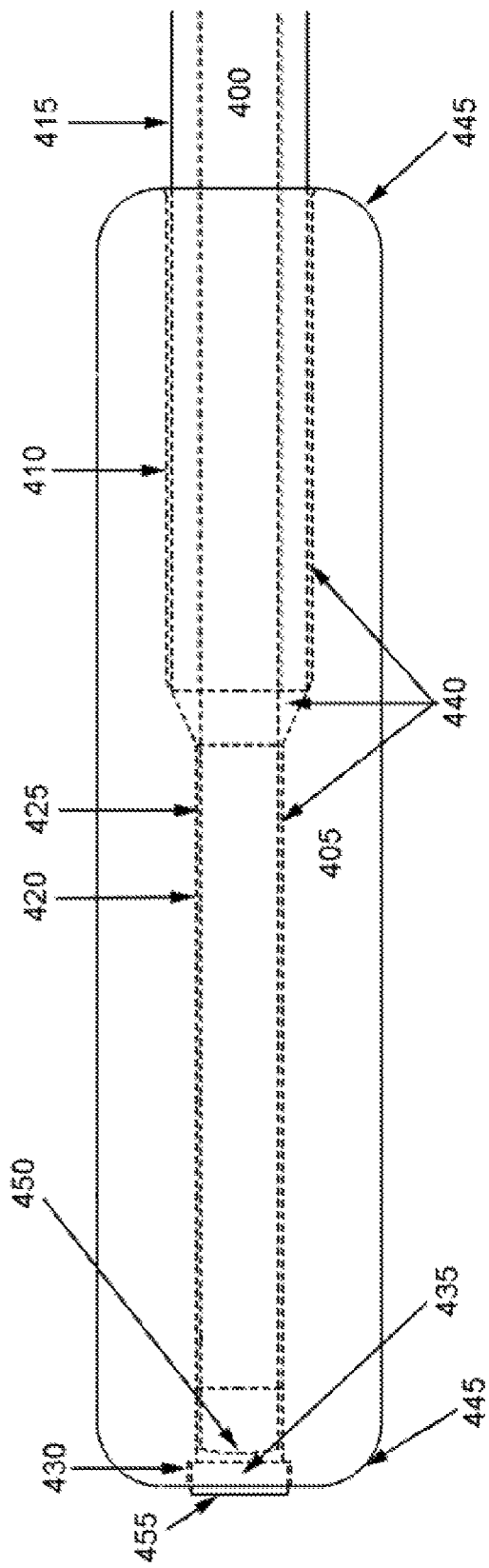
FIG. 7 is a preferred embodiment of the invention that utilizes a refractory, crystalline and UV/visible/infrared transparent window for displacing absorbing media.

A additional embodiment of the invention is presented in FIG. 7. A protective ferrule or ferrule 405, similar to those discussed before, is produced with three bore diameters; one bore 410 at approximately 450 μm accommodates the nylon or EFTE (or Hytrel or other common fiber optic buffer polymer) diameter 415 of the fiber 400, a second bore 420 at approximately 275 μm accommodates the FA coated fiber 425, and a third bore 430 at approximately 350 μm accommodates a polished section of sapphire optical fiber 435. The fiber 400 is glued 440 within the ferrule 405 within the buffer bore, the transition chamfer and the FA bore. The ferrule is half filleted 445 at each end for easy passage through a deflected ureteroscope. In the illustration, the fiber output surface 450 is slightly convex to quasi-collimate/focus the emerging laser light, although this is not a requirement for this embodiment.

The themes of this invention remain the displacement of the water column between the fiber and the target for more efficient coupling of the laser energy to the target stone, and the avoidance of the rapid burn back phenomenon seen in small laser lithotripsy fibers that reduces surgical efficiency by approximately 40% to 50% within the first minute or two of surgery. While the devitrification issues are addressed in earlier embodiments through larger mass target contact components (where silica ferrules are utilized) or through the use of refractory and devitrification resistant, crystalline and polycrystalline (ceramic) materials, in the embodiment depicted in FIG. 7, the devitrification labile silica ferrule (if silica) is shielded from target contact by a slight protrusion 455 of the sapphire window as well.

Figure 8:
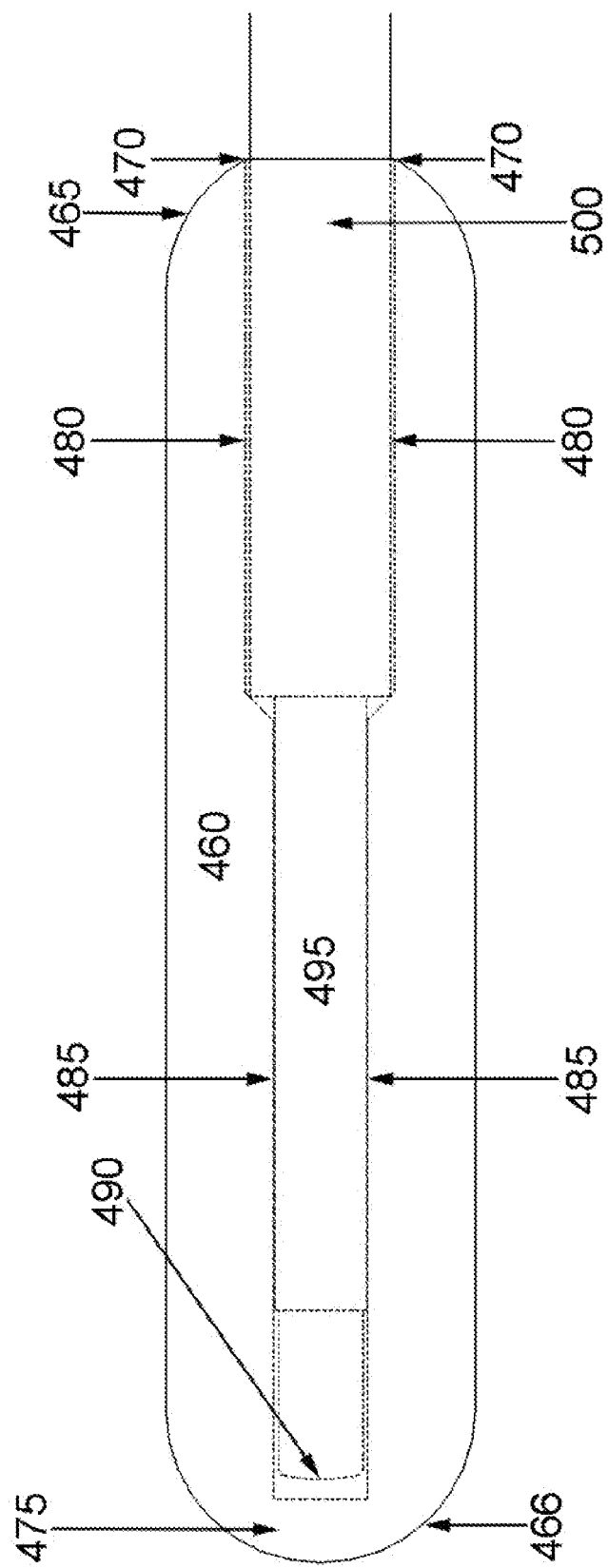
FIG. 8 is a preferred embodiment of the invention utilizing a refractory, crystalline and UV/visible/infrared transparent capsule (cap).

An additional embodiment, depicted in FIG. 8, simplifies the process of producing a closed-end 475 capsule 460 by forming the ferrule consisting entirely of sapphire (as compared to FIG. 7). The proximal 465 and distal 466 ends are, preferably, filleted (or chamfered) for smooth passage through the ureteroscope channel. The capsule end (opposite the closure 475) is open 470 and of an appropriate diameter bore 480 to accommodate the fiber buffer diameter 500. A second bore 485 is of an appropriate diameter to accommodate the fiber first polymer coating 495. The output surface 490 of the fiber is depicted as curved for reduced divergence but may be flat. The ferrule's second bore 485, preferably, ends at a closed-end output region or lens 475. The lens 475 preferably includes a flat interior surface (adjacent to the borehole) and either a flat or convex exterior surface. In one instance, the lens 475 includes a convex exterior surface that is congruous with the fillet 466 of the curved ferrule surface. In another instance, the fiber tip 490 has a convex lens that when combined with the exterior convex lens 475 on the sapphire ferrule, provides a collimated or approximately collimated beam immediately distal to the assembly for extremely efficient energy deliver to stone targets. That is, the fiber output surface and the ferrule lens cooperatively focus the beam on the surgical target. As in prior embodiments, the fiber can be retained within the capsule by means of adhesive within the bores.

In another embodiment, depicted in FIG. 9, the ferrule can be affixed to the fiber with a crimp connector. This crimp connector can be employed in all embodiments that utilize non-metallic ferrules or caps (described above). For ease of explanation, FIG. 9 depicts a sapphire ferrule 505 that is similar to the ferrule in FIG. 8 but upon which a stepped and smaller outer diameter 510 is disposed. The smaller outside diameter 510 is preferably affixed within a borehole 515 of a metallic, crimp connector 530, where the two mating surfaces are bonded by means known in the art (e.g., adhesive bonding). The crimp connector, preferably, includes a second and smaller inside diameter 520 which accept the fiber buffer. In another instance, the crimp connector can have a single borehole (single inside diameter) where the sapphire ferrule has a smaller outside diameter that is approximately the same diameter as the fiber buffer outside diameter.

The fiber is fixed within the ferrule 535 borehole by an adhesive while it is fixed within the crimp connector 520 by crimping 525 (crimp indentations are shown absent the fiber). The optical functionality remains unaltered with respect to the embodiment in FIG. 8, but the sapphire ferrule is, preferably, retained on the fiber by two separate mechanisms for security.

What is claimed:

1. A optical fiber output termination comprising:
    an optical fiber having
        a core composed of fused silica or doped fused silica, a cladding disposed about the core, a first polymer coating disposed about the cladding, and a second polymer coating disposed about the first polymer coating,
        an output terminus, and
        a stripped terminus coincident with the output terminus, the stripped terminus including the core, cladding, and the first polymer coating, a stripped terminus length, and an outside diameter; and
    a ferrule affixed to the stripped terminus, having a length longer than the stripped terminus length, and a borehole, the borehole having a first bore with an inside diameter substantially similar to the outside diameter of the stripped terminus, where an output face carried on the output terminus is within the bore of the ferrule, the output face positioned at a fiber setback relative to a terminus of the ferrule at a distance where the highest angle of emitted radiation does not impinge upon the ferrule borehole;
wherein the $$\text{fiber setback} < \frac{0.5(\text{first bore diameter} - \text{fiber cladding diameter})}{\tan(\text{fiber Output Angle})};$$

$$\text{fiber Output Angle} = \arcsin(\text{fiber Numerical Aperture});$$

$$\text{fiber Numerical Aperture} = \sqrt{(\text{core } RI)^2 - (\text{cladding } RI)^2};$$

wherein RI is refractive index.

2. The optical fiber output termination of claim 1, where the ferrule is fused quartz, fused silica, single crystal sapphire, a metal oxide ceramic, a silicon carbide, a thermoset polymer, a metal, an alloy, or a mixture thereof.

3. The optical fiber output termination of claim 1, where the borehole includes a second bore that has an inside diameter that is substantially similar to a second polymer coating outside diameter; wherein the ferrule is affixed about the second polymer coating and within the second bore.

4. The optical fiber output termination of claim 3, further comprising a third bore having a third inside diameter.

5. The optical fiber output termination of claim 4, wherein the third bore is adjacent to the terminus of the ferrule, the output termination further comprising a window of crystalline material transparent to infrared radiation disposed within the third bore and extending beyond the terminus of the ferrule.

6. The optical fiber output termination of claim 1, where the output terminus includes an output surface that is flat.

7. The optical fiber output termination of claim 1, where the output terminus includes an output surface that is convex.

8. The optical fiber output termination of claim 1 further comprising a window of crystalline material transparent to infrared radiation disposed at the terminus of the ferrule.

9. The optical fiber output termination of claim 8, wherein the window of crystalline material extends beyond the terminus of the ferrule.

10. The optical fiber output termination of claim 8, wherein the window of crystalline material consists of sapphire.

11. The optical fiber output termination of claim 1, wherein the optical fiber and affixed ferrule are disposed within a fluid transfer tube; wherein the terminus of the ferrule extends beyond a terminus of the fluid transfer tube.

12. The optical fiber output termination of claim 11, wherein the fluid transfer tube includes a plurality of lumen in fluidic contact with the ferrule.

13. The optical fiber output termination of claim 1, wherein the borehole includes a setback surface, the setback surface carried on an inside diameter along the fiber setback; the setback surface carrying a hydrophobic or super-hydrophobic surface that provides a contact angle of at least 90°.

14. A optical fiber output termination comprising:
    an optical fiber having a silica core, a cladding disposed about the core, a first polymer coating disposed about the cladding, and a second polymer coating disposed about the first polymer coating, the second polymer coating having an outside diameter, an output terminus, and a hydrophilic-stripped terminus coincident with the output terminus, the hydrophilic-stripped terminus including the core and cladding, a hydrophilic-stripped terminus length, and an outside diameter;

a ferrule affixed to the stripped terminus, having a length longer than the hydrophilic-stripped terminus length, and a borehole, where an output face carried on the output terminus is within the borehole of the ferrule, the output face positioned at a fiber setback relative to a terminus of the ferrule at a distance where the highest angle of emitted radiation does not impinge upon the ferrule borehole, the borehole having a first bore and a second bore, the first bore having an inside diameter substantially similar to the outside diameter of the hydrophilic-stripped terminus, the second bore having an inside diameter substantially similar to the outside diameter of the second polymer coating; and a moisture-sensitive, gas-generating charge that is in fluidic communication with the output terminus of the fiber, carried between the ferrule and the optical fiber; wherein the $$\text{fiber setback} < \frac{0.5(\text{first bore diameter} - \text{fiber cladding diameter})}{\tan(\text{fiber Output Angle})};$$

$$\text{fiber Output Angle} = \arcsin(\text{fiber Numerical Aperture});$$

$$\text{fiber Numerical Aperture} = \sqrt{(\text{core } RI)^2 - (\text{cladding } RI)^2};$$

and wherein RI is refractive index.

15. A optical fiber output termination of claim 14, wherein the gas-generating charge is affixed within the borehole, the gas-generating charge having an outside diameter coincident with the second bore and a charge borehole that has an inside diameter that is a substantially similar to the first bore of the ferrule;

wherein the optical fiber is hermetically affixed to the ferrule within the second bore.

16. A optical fiber output termination of claim 14, wherein the bore hold includes an intermediate bore, wherein the gas-generating charge is affixed within the intermediate bore, has an outside diameter coincident with the intermediate bore and a charge borehole that has an inside diameter that is a substantially similar to the first bore of the ferrule;

wherein the hydrophilic-stripped terminus passes through the gas-generating charge borehole.

17. A optical fiber output termination comprising:

an optical fiber having a silica core, a cladding disposed about the core, a first polymer coating disposed about the cladding, and a second polymer coating disposed about the first polymer coating, the second polymer coating having an outside diameter, an output terminus, and a stripped terminus coincident with the output terminus, the stripped terminus including the core and cladding, a stripped terminus length, and an outside diameter;

a ferrule consisting of sapphire, affixed to the stripped terminus, having a length longer than the stripped terminus length, and a borehole, where an output face carried on the output terminus is within the borehole of the ferrule, the output face positioned at a fiber setback relative to a terminus of the ferrule, the ferrule carrying a lens having a flat input surface adjacent to the borehole and a convex or flat output surface; wherein the fiber output face and the ferrule lens provide a beam path that culminates at a position immediately distal to the ferrule lens;

wherein the $$\text{fiber setback} < \frac{0.5(\text{first bore diameter} - \text{fiber cladding diameter})}{\tan(\text{fiber Output Angle})};$$

$$\text{fiber Output Angle} = \arcsin(\text{fiber Numerical Aperture});$$

$$\text{fiber Numerical Aperture} = \sqrt{(\text{core } RI)^2 - (\text{cladding } RI)^2};$$

and wherein RI is refractive index.

* * * * *